United States Patent [19]

Ruderian

[11] Patent Number: 4,596,565
[45] Date of Patent: Jun. 24, 1986

[54] SALVE APPLICATOR

[76] Inventor: Max J. Ruderian, 454 Hanley Ave., Los Angeles, Calif. 90049

[21] Appl. No.: 701,745

[22] Filed: Feb. 14, 1985

[51] Int. Cl.⁴ .............................................. A61F 7/00
[52] U.S. Cl. .................................... 604/291; 128/399
[58] Field of Search ................ 604/291; 128/368, 399, 128/402

[56] References Cited

U.S. PATENT DOCUMENTS

| | | | |
|---|---|---|---|
| 1,825,118 | 9/1931 | Jaeg ...................................... | 128/399 |
| 2,267,547 | 12/1941 | Zimmerman ......................... | 604/291 |
| 2,787,998 | 4/1957 | Grossi et al. ...................... | 604/291 X |
| 3,861,364 | 1/1975 | Greenfeld ............................ | 128/368 |

Primary Examiner—John D. Yasko
Attorney, Agent, or Firm—Pastoriza, Kelly & Lowry

[57] ABSTRACT

The applicator comprises a portable hand-held blower motor with heating wires to provide a stream of heated air out an exit opening. A porous support element covers the exit opening and a fabric material is arranged to be draped about the porous support element to provide a cushioned surface for engaging a body portion. This fabric material is impregnated with a medicant so that the heated air from the blower opens up the pores of the body portion engaged by the fabric and the medicant is easily absorbed thereby bringing relief to victims of arthritis and other aches and pains.

11 Claims, 6 Drawing Figures

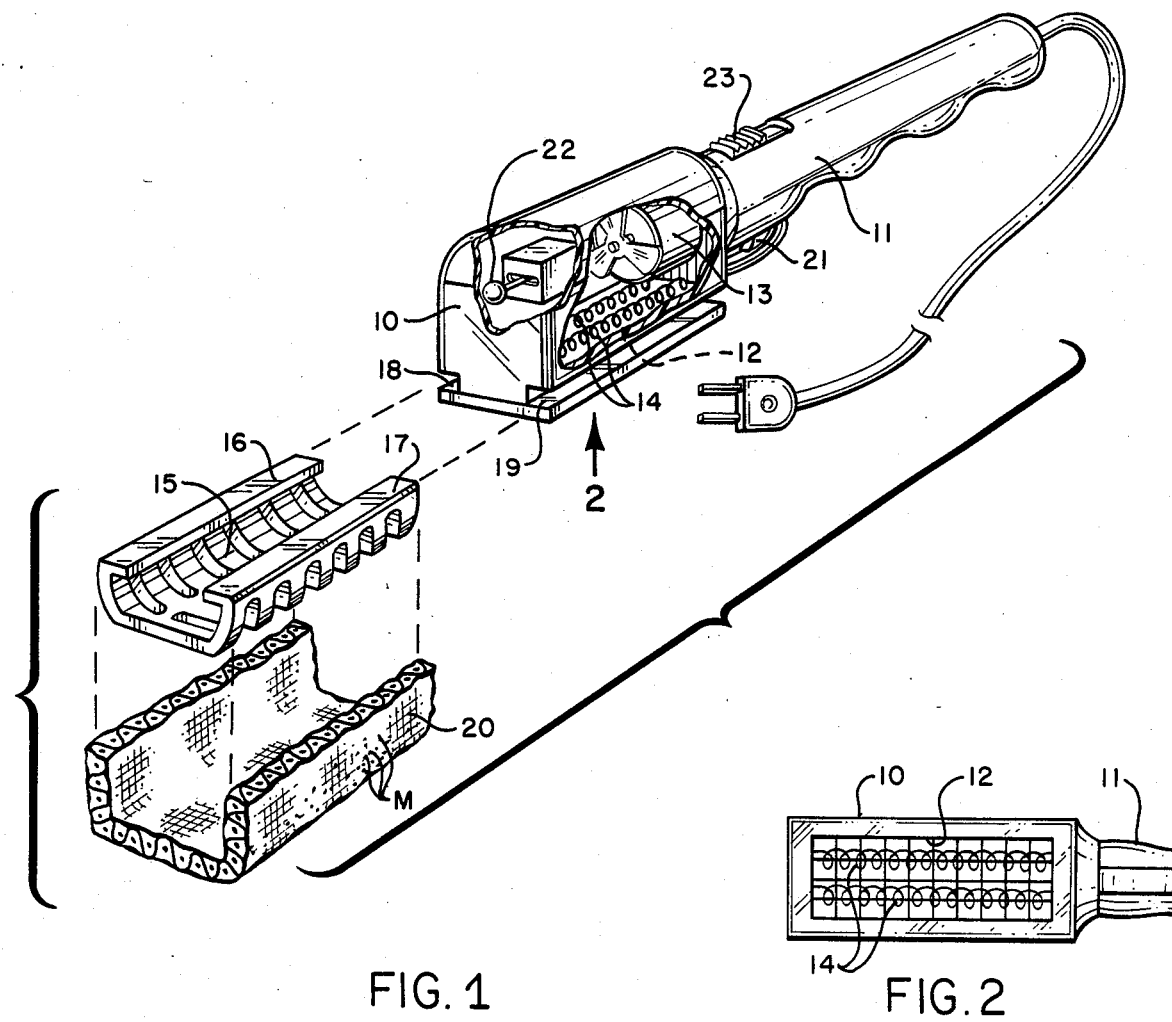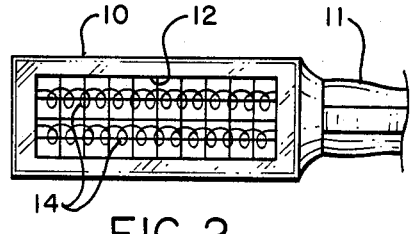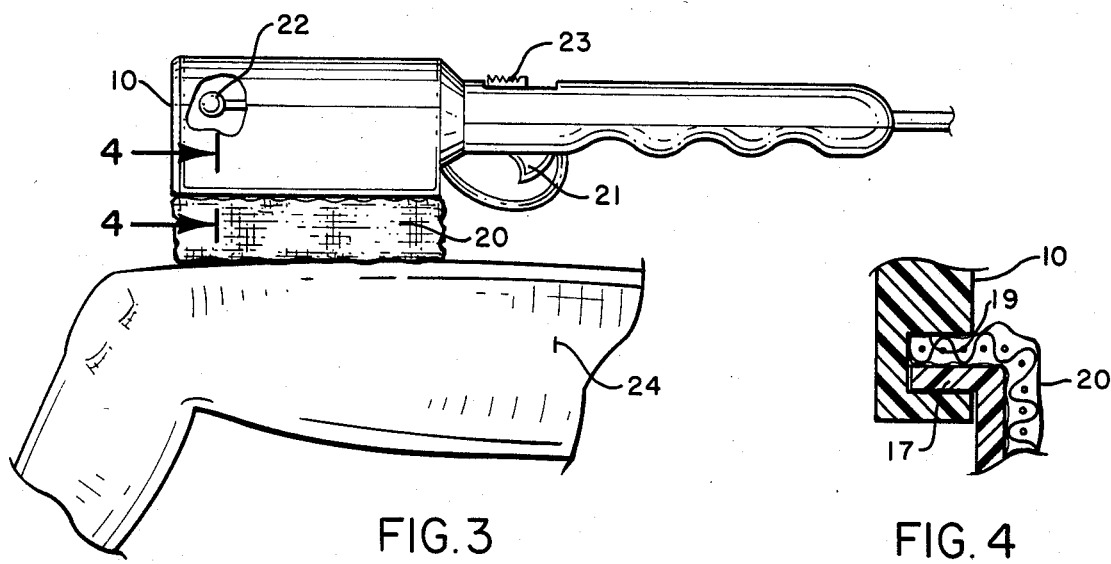
FIG. 1
FIG. 2
FIG. 3
FIG. 4

SALVE APPLICATOR

FIELD OF THE INVENTION

This invention relates generally to applicators and more particularly to an improved applicator for applying salve-like medicants to a body portion for relieving aches and pains.

BACKGROUND OF THE INVENTION

Many salves are available on the market sometimes in semi-viscous form or even liquid form for rubbing over body portions to relieve aches and pains. Usually the salve is applied by using a cotton swab or gauze pad and simply manually rubbing the medicant into the pores of the skin on the body portion afflicted. The medicant itself often provides a soothing effect and the effect of heating the area involved.

BRIEF DESCRIPTION OF THE PRESENT INVENTION

The present invention has to do with an applicator for salve to relieve aches and pains wherein there is provided a stream of heated air which is directed at the body portion afflicted thereby enabling the medicant to be more readily absorbed.

In accord with the invention in its broadest aspect, the salve applicator includes a portable hand-held casing having an air exit opening. A blower motor is incorporated in this casing along with a heating means. The motor and heating means are positioned to provide a stream of heated air out the exit opening when operated. A porous support element is positioned adjacent to the exit opening. A fabric material covers this support element to provide a cushioned surface for application to a body portion. The heated air from the exit opening and engagement of the cushioning surface functions to heat the area and soothe the body portion.

A salve or medicant is impregnated within the fabric material so that the same is readily transferred to the body portion through the skin pores under influence of the heated air stream.

In preferred embodiments of the invention, the casing includes a vibrating element which will aid in moving the cushioned surface over the afflicted body portion area to be treated.

BRIEF DESCRIPTION OF THE DRAWINGS

A better understanding of this invention will be had by now referring to the accompanying drawings in which:

FIG. 1 is an exploded perspective view partly broken away of one embodiment of the invention;

FIG. 2 is a fragmentary view looking in the direction of the arrow 2 of FIG. 1;

FIG. 3 is a side elevational view of the applicator illustrating the actual use of the same;

FIG. 4 is a fragmentary cross-section taken in the direction of the arrows 4—4 of FIG. 3;

DETAILED DESCRIPTION OF THE INVENTION

Figure 5:
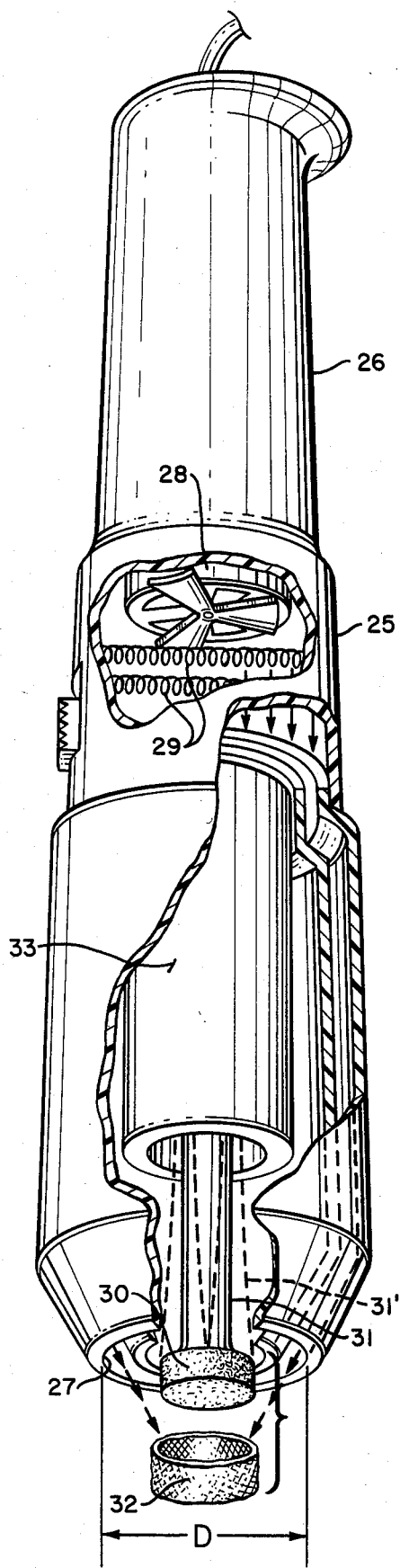
FIG. 5 is a broken away perspective view of a preferred embodiment of the invention; and, FIG. 6 is an exploded view of preferred substitute components for use in the embodiment of FIG. 5.

Referring first to FIG. 1, the salve applicator includes a portable hand-held casing 10 having a handle portion 11 and an air exit opening on the bottom side indicated at 12.

A blower motor 13 is incorporated in the casing along with heating means schematically indicated by the wires 14. The motor and heating means are so positioned within the casing as to provide a stream of heated air out of the exit opening 12 when operated.

Still referring to FIG. 1, there is shown exploded away from the casing 10 in the forward portion of the drawing a porous support element 15 which may take the form of a plastic frame having elongated openings as shown. Porous element 15 includes inturned flanges 16 and 17 for reception in channels 18 and 19 formed in the lower portion of the casing 10 so that the porous support element is positioned adjacent to the exit opening 12. In the embodiment of FIG. 1, this porous element essentially covers the exit opening 12.

Cooperating with the porous support element is a fabric material 20 shown exploded below the support element 15. This fabric material is arranged to cover the support element and provide a cushioned surface for application to a body portion. The heated air from the exit opening and engagement of the cushioned surface will soothe the body portion.

In the preferred embodiment, the fabric 20 is impregnated with a medicant or salve indicated by the letter M.

Referring again to the casing portion in FIG. 1, there is provided an on/off switch 21 beneath the forward portion of the handle 11 for operating the blower 13 and heater 14. In addition, the upper portion of the casing 10 houses a vibrating element 22. This element is independently operable by a switch 23 permitting it to be turned on and off independently of the operation of the blower motor. The vibrating element will essentially vibrate the casing and thereby facilitate the absorption of the medicant into the pores of the body portion when the applicator is in use.

FIG. 2 shows the underside of the casing 10 wherein the exit opening 12 and heating wires 14 are clearly visable.

Referring now to FIG. 3, the applicator is shown in assembled relationship with the cushioned surface of the fabric 20 in engagement with a body portion 24 which might be a person's thigh.

In the operation of the device, warm air will pass through the porous support 15 described in FIG. 1 and fabric 20 directly to the pores of the skin of the body portion 24 thereby tending to open up the pores so that the medicant M in the fabric 20 can be appropriately and easily absorbed. When the vibrator 22 is operated by the switch 23, the back and forth vibrations will be transmitted to the fabric 20 thereby greatly aiding the absorption process as a consequence of the back and forth massaging action resulting from the vibrating element.

The fabric 20 can be removed from the support element 15 and a fresh fabric substituted.

Any appropriate means may be provided for holding the fabric to the support element. With particular reference to FIG. 4, it will be noted in the embodiment of FIGS. 1–3 the fabric is held by folding over the opposite marginal edges into the channels such as the channel 19, the marginal edge being indicated at 20'. The fabric will thus be frictionally retained by the channels 18 and 19 described in FIG. 1.

Referring now to FIG. 5, there is shown another embodiment of the invention again including a casing 25 with handle 26. The casing includes at its lower end as shown in FIG. 5 an annular conical exit opening 27 for heated air. This heated air is provided by a blower motor 28 incorporated in the casing 25 and heating wires 29.

In the central portion of the annular conical exit opening 27 for the heated air, there is a sponge like porous support element 30 detachably secured to the end of a shaft 31. A fabric material 32, in turn, is shown exploded away from the element 30. As in the other embodiments, this fabric can be impregnated with a medicant M. Shaft 31 actually constitutes the vibrating element of a vibrator 33 centrally positioned in the overall casing structure.

In the embodiment of FIG. 5, the heated air will heat the skin area surrounding the fabric 32, the conical exit 27 focusing the airflow onto the body portion. The fabric can then be placed into engagement with a heated skin area and again the medicant will be absorbed. The vibrator can be actuated to orbit the shaft end between the phantom line position 31' thereby messaging the skin and aiding absorption. By holding the applicator in a manner so that the fabric is spaced away from the area, only the heated air will treat the area and the application of air alone might be sufficient to bring relief. In this latter event, the vibrator would not be used. When the vibrator is used, the porous support element will orbit and intercept some of the heated air from the conical exit 27 so that this air will pass through the fabric and help in absorption of the medicant.

The fabric 32 and support provides a smaller surface area than the fabric 20 described in FIG. 1. This small area will permit a person to reach around various Joints which might not be as readily accessible to a larger cushioned surface area.

Figure 6:
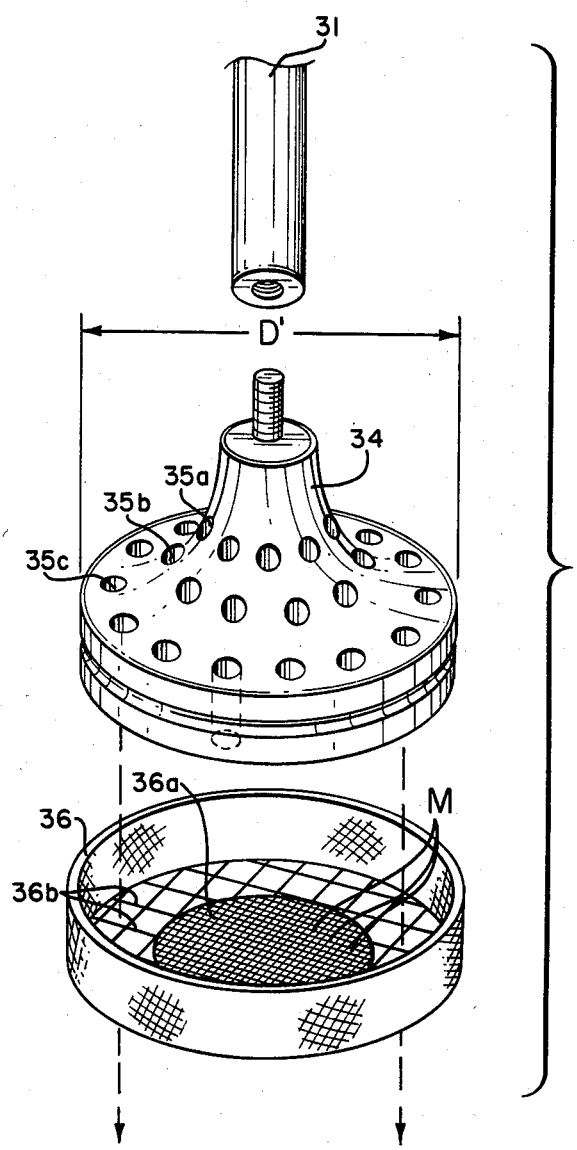

FIG. 6 illustrates the manner in which a preferred support element somewhat larger than the support element 30 of FIG. 5 can be substituted together with a larger fabric of unique construction.

More particularly, a larger support element is shown at 34 and in this instance, rather than a sponge-like element, constitutes a hollow plastic housing with circular rows of vertical openings 35a, 35b and 35c passing therethrough and out the bottom.

Shown exploded below the support element 34 is a fabric material 36 of cup shape to fit over and be held frictionally by the support element 34. Fabric 36 may be impregnated with a medicant M. It will be noted that the fabric has a dense central portion 36a the periphery of which is supported by a less dense or almost net-like fabric material 36b.

Referring back to FIG. 5, if the outside diameter of the annular exit for the hot air is D, then by making the outside diameter D' of the support element 34 the same as or greater than D, the periphery of the support and fabric will overlie the annular exit opening so that heated air will pass through the openings 35a, 35b and 35c and thence through the fabric 36 in the same manner as heated air pssed through the fabric 20 in the embodiment of FIG. 1. In this respect, however, air from the outer row of openings 35c will pass through the net support part of the fabric 36b directly onto the body portion being treated while air through the openings 35a. and 35b will pass through the dense portion of the fabric 36a to help in absorption of the medicant.

As shown in FIG. 6, the support element 34 is detachably secured to the shaft 31 as by a screw 37 and tapped opening 38 in the end of the shaft. While either the porous sponge-like support 30 or the larger plastic housing support 34 can be used on the end of the shaft 31, in the preferred embodiment, the support 34 is used to provide for the most satisfactory all around use.

Changes falling within the scope and spirit of this invention will occur to those skilled in the art. The salve applicator is therefore not to be thought of as limited to the specific embodiments set forth for illustrative purposes.

I claim:

1. A salve applicator including, in combination:
    (a) a portable hand-held casing having an air exit opening
    (b) a blower motor in said casing;
    (c) a heating means in said casing, said motor and said heating means being positioned to provide a stream of heated air out said exit opening when operated;
    (d) a porous support element positioned adjacent to said exit opening, said porous support element comprising a hollow plastic housing with circular rows of vertical openings passing therethrough and out the bottom; and
    (e) a fabric material covering said support element to provide a cushioned surface for application to a body portion, said fabric material covering the bottom of said housing and having a central dense portion for containing a medicant and a net-like outer portion supporting the periphery of said central portion, the heated air from said exit opening and engagement of said cushioned surface soothing the body portion, said heated air passing through at least the outermost row of said vertical openings and through said net-like portion of the fabric material to heat the body portion being treated, the heated air passing through the remaining vertical openings passing through said central dense portion of the fabric material to assist in absorption of the medicant.

2. An applicator according to claim 1, including a vibrating element incorporated in said casing for vibrating the applicator and thereby facilitating the absorption of medicant into the pores of the body portion.

3. An applicator according to claim 2, including a switch permitting the turning on and off of said vibrating element independently of the operation of said blower motor.

4. An applicator according to claim 3, in which said porous support element covers said exit opening so that said heated air passes through said fabric material to the body portion engaged thereby.

5. An applicator according to claim 3, in which said porous support element is detachably connected to the casing whereby it can be easily manually removed and replaced by a support element of a different size.

6. An applicator according to claim 1, in which said porous support element comprises a sponge-like substance through which air can pass.

7. An applicator according to claim 1, in which said exit opening is conically shaped to focus the air flow onto said body portion.

8. A vibratory applicator including, in combination:
    (a) a portable hand-held casing having an air exit opening;
    (b) a blower motor in said casing;

(c) heating means in said casing, said motor and said heating means being positioned to provide a stream of heated air out said exit opening when operated; and (d) a vibrator mounted within said casing and including an externally exposed vibratory massage element positioned substantially at said exit opening for application to a body portion whereby the stream of heated air through said exit opening flows directly around and about said vibratory element to cooperate with said vibratory element in providing a soothing effect to the body portion.

9. The applicator according to claim 8, in which said vibratory element is impregnated with a medicant such that the medicant can be absorbed into the pores of the body portion engaged by thge vibratory element and heated by said heated air stream to thereby relieve aches and pains.

10. An applicator according to claim 8, including a switch permitting the turning on and off of said vibratory element independently of the operation of said blower motor.

11. The applicator according to claim 9, in which said vibrartory element includes a porous element covering said exit opening so that said heated air passes through said porous element.

* * * * *